United States Patent [19]

Mihailovski

[11] 4,115,581

[45] Sep. 19, 1978

[54] BIS-STANNANE INSECTICIDES

[75] Inventor: Alexander Mihailovski, Kensington, Calif.

[73] Assignee: Stauffer Chemical Company, Westport, Conn.

[21] Appl. No.: 858,984

[22] Filed: Dec. 9, 1977

[51] Int. Cl.² ............................................... A01N 9/00
[52] U.S. Cl. .................................. 424/288; 260/429.7
[58] Field of Search ...................... 424/288; 260/429.7

[56] References Cited

U.S. PATENT DOCUMENTS

| | | | |
|---|---|---|---|
| 3,264,177 | 8/1966 | Kenaga | 424/288 |
| 3,542,824 | 11/1970 | Bublitz | 260/429.7 |
| 3,609,173 | 9/1971 | Kushlefsky et al. | 424/288 X |

FOREIGN PATENT DOCUMENTS 107,331 10/1974 Japan.

*Primary Examiner*—Allen J. Robinson
*Attorney, Agent, or Firm*—M. Henry Heines

[57] ABSTRACT

Compounds having the formula

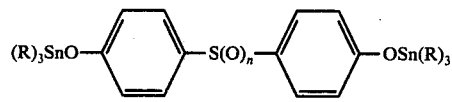

in which R is cyclohexyl or alkyl having 2 to 6 carbon atoms, and $n$ is 0, 1, or 2, are active as insecticides.

7 Claims, No Drawings

BIS-STANNANE INSECTICIDES

BRIEF DESCRIPTION OF THE INVENTION

This invention relates to insecticidal compounds, compositions and methods of use. The compounds and compositions are particularly useful as miticides.

The compounds of the present invention have the following formula:

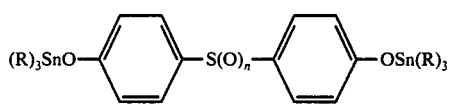

wherein R is cyclohexyl or alkyl having 2 to 6 carbon atoms, and $n$ is 0, 1, or 2. In a preferred embodiment, R is cyclohexyl or n-butyl, and $n$ is 0, 1, or 2. In a more preferred embodiment, R is cyclohexyl or alkyl having 2 to 6 carbon atoms and $n$ is 0. In a particularly preferred embodiment, R is cyclohexyl and $n$ is 0, 1, or 2. All carbon atom ranges herein are intended to be inclusive of their upper and lower limits.

These compounds are useful as insecticides, particularly in the control of mites, when used in an insecticidally effective amount.

By "insecticidally effective amount" is meant the amount of the herein disclosed insecticidal compounds which when applied in any conventional manner to the habitat of insects, the feedstuffs of insects, or the insects themselves, will kill or substantially injure a significant portion thereof.

DETAILED DESCRIPTION OF THE INVENTION

The compounds of the present invention can be prepared by reacting either 4,4'-thiodiphenol, 4,4'-sulfinyldiphenol, or 4,4'-sulfonyldiphenol, with an appropriately substituted tin compound. The tin compound can be any of the following:

(1) a trialkyl tin halide in the presence of a base acceptor such as sodium hydride;

(2) a trialkyl tin hydroxide in the presence of an acid catalyst and an inert solvent, for example benzene or toluene, for azeotropic dehydration; or (3) a bis-trialkyl tin oxide in the presence of an acid catalyst and inert solvent as in (2) above.

The following examples are offered to illustrate the manufacture of the compounds of the present invention, and are not intended to place any limitations on the scope of the invention.

EXAMPLE 1

4,4'-bis-(Tricyclohexylstannoxy)-diphenylsulfide

A 200 milliliter flask was charged with 1.5 grams (0.060 mole) of sodium hydride, 50 milliliters of tetrahydrofuran, and 5.0 grams (0.023 mole) of 4,4'-thiodiphenol. To this was added in dropwise manner 18.1 grams (0.045 mole) of tricyclohexyl tin chloride dissolved in 30 milliliters of tetrahydrofuran. The mixture was stirred overnight at ambient temperature. The solvent was evaporated and the residue treated with 100 milliliters benzene and 50 milliliters water. The benzene solution was separated from the aqueous layer and the solvent evaporated to yield 18.5 grams of a colorless solid, with melting point 123°–126° C. Analysis by nuclear magnetic resonance (NMR) and mass spectrometry (MS) showed the structure to be that of the title compound.

EXAMPLE 2

4,4'-bis-(Tricyclohexylstannoxy)-diphenylsulfone

The procedure of Example 1 was followed, using 5.8 grams (0.023 mole) of 4,4'-sulfonyldiphenol and 18.1 grams (0.045 mole) of tricyclohexyl tin chloride. Product recovery yielded 17.0 grams of a white solid, with melting point 149°–153° C. Analysis by NMR and MS showed the structure to be that of the title compound.

EXAMPLE 3

4,4'-bis-(Tributylstannoxy)-diphenylsulfide

The procedure of Example 1 was followed, using 5.0 grams (0.023 mole) of 4,4'-thiodiphenol and 14.6 grams (0.045 mole) of tributyl tin chloride. Product recovery yielded 15.3 grams of a yellow liquid identified by NMR and MS analysis as the title compound.

EXAMPLE 4

4,4'-bis-(Tributylstannoxy)-diphenylsulfone

The procedure of Example 1 was followed, using 5.8 grams (0.023 mole) of 4,4'-sulfonyldiphenol and 14.6 grams (0.045 mole) of tributyl tin chloride. Product recovery yielded 7.0 grams of a yellow liquid, identified by NMR analysis as the title compound.

The structural formulas for these examples are shown in Table I.

TABLE I

| Example | Formula | Physical Properties Melting point (° C) |
| --- | --- | --- |
| 1 | [(cyclohexyl)₃]–SnO–C₆H₄–S–C₆H₄–OSn–[(cyclohexyl)₃] | 123–126 |
| 2 | [(cyclohexyl)₃]–SnO–C₆H₄–S(O)₂–C₆H₄–OSn–[(cyclohexyl)₃] | 149–153 |

TABLE I-continued

| Example | Formula | Physical Properties Melting point (° C) |
|---|---|---|
| 3 | (n-C$_4$H$_9$)$_3$SnO—⟨C$_6$H$_4$⟩—S—⟨C$_6$H$_4$⟩—OSn(n-C$_4$H$_9$)$_3$ | liquid |
| 4 | (n-C$_4$H$_9$)$_3$SnO—⟨C$_6$H$_4$⟩—S(=O)$_2$—⟨C$_6$H$_4$⟩—OSn(n-C$_4$H$_9$)$_3$ | liquid |

The compounds listed in Table I were evaluated for insecticidal activity according to the following procedures.

INSECTICIDE EVALUATION

A. Housefly [*Musca domestica* (L.)]

The test compound is diluted in acetone and an aliquot is pipetted onto the bottom of a 55 × 15 millimeter aluminum dish. To insure even spreading on the bottom of the dish, one milliliter of acetone containing 0.02% peanut oil is added. After all the solvent has evaporated, the dish is placed in a circular cardboard cage containing 25 one-day-old female houseflies. The cage is covered on the bottom with cellophane and the top with tulle netting, and contains a sugar-water saturated cotton plug for maintenance of the flies. Mortality is recorded after 48 hours. The primary screening level for this test is 100 micrograms of the test compound per 25 female houseflies.

B. Lygus bug [*Lygus hesperus* (Knight)]

The test compound is dissolved in a 50—50 acetone-water solution. Two cubic centimeters of the solution are sprayed through a DeVilbiss-type EGA hand spray gun into a circular cardboard cage covered on the bottom with cellophane and the top with tulle netting, containing one string bean pod and ten adult lygus bugs. Percent morality is recorded after 48 hours. The primary screening level for this test is 0.05% by weight of the test compound in the acetone-water solution.

C. Direct Spray Assay on Black Bean Aphid [*Aphis fabae* (Scop.)]

A nasturtium plant (*Tropaeolum sp.*), approximately 5 centimeters tall, is transplanted into sandy loam soil in a 3-inch clay pot and infested with 25-50 black bean aphids of mixed ages. Twenty-four hours later the plant is sprayed, to the point of runoff, with a 50—50 acetone-water solution of the test chemical. The treated plant is held in the greenhouse and mortality is recorded after 3 days. The primary screening level for this test is 0.05% by weight of the test compound in the acetone-water solution.

D. Direct Spray Assay on Green Peach Aphid [*Myzus persicae* (Sulzer)]

A radish plant (*Rhaphanus sativus*), approximately 2 centimeters tall, is transplanted into sandy loam soil in a 3-inch clay pot and infested with 25-50 green peach aphids of mixed ages. Twenty-four hours later the plant is sprayed, to the point of runoff, with a 50—50 acetone-water solution of the test compound. The treated plant is held in a greenhouse and mortality is recorded after 3 days. The primary screening level for this test is 0.05% by weight of the test compound in the acetone-water solution.

E. Salt-marsh Caterpillar [*Estigmene acrea* (Drury)]

A test solution is prepared by dissolving the test compound in a 50—50 acetone-water solution. A section of a curly dock (*Rumex crispus*) leaf, approximately 2.5 centimeters wide and 4 centimeters long, is immersed in the test solution for 2-3 seconds, then placed on a wire screen to dry. The dried leaf is placed in a petri dish containing a moistened piece of filter paper, and infested with five second-instar salt-marsh caterpillar larvae. Mortality of the larvae is recorded 48 hours later. If surviving larvae are still present, a piece of synthetic media is added to the dish and the larvae are observed for an additional five days in order to detect delayed effects of the test compound. The primary screening level for this test is 0.05% by weight of the test compound in the solution.

F. Cabbage Looper [*Trichoplusia ni* (Hübner)]

The procedure for cabbage looper larvae is the same as that used for salt-marsh caterpillar larvae, except that a cotyledon of hyzini squash (*Calabacita abobrinha*) of approximately the same size as the curly dock leaf section is used in place of the latter. The primary screening level for this test is 0.1% by weight of the test compound in the solution.

G. Tobacco Budworm [*Heliothis virescens* (F.)]

Larvae of the tobacco budworm are used in this test in a procedure identical to that used for salt-marsh caterpillar larvae, except that a Romaine lettuce (*Latuca sativa*) leaf section of approximately the same size as the curly dock leaf section is used in place of the latter. The primary screening level for this test is 0.1% by weight of the test compound in the solution.

H. Two-Spotted Mite [*Tetranychus urticae* (Koch)]

A pinto bean plant (*Phaseolus sp.*), approximately 10 centimeters tall is transplanted into sandy loam soil in a 3-inch clay pot and infested with two-spotted mites of mixed ages and sexes. Twenty-four hours later the infested plants are inverted and dipped for 2-3 seconds in a 50—50 acetone-water solution of the test compound.

The treated plant is held in a greenhouse for 7 days. Mortality is then determined for both the adult mites and the nymphs hatching from eggs which were on the plants at the time of treatment. The primary screening level for this test is 0.05% by weight of the test compound in the acetone-water solution.

Table II is a summary of the results of tests performed on the compounds of Table I. These test results are expressed as $LD_{50}$ values, which represent the dose of test compound which was lethal to 50% of the insect population in the test. The entries in Table II were obtained as follows:

For a particular insect, each compound was initially tested at the primary screening level. Those compounds showing less than 50% kill at this level are represented in the table by the primary screening level preceded by a "greater than" sign (>). Those compounds showing approximately 50% kill are represented by the primary screening level alone. Those compounds showing greater than 50% kill were subjected to further testing at successively lower levels, until the level was found at which approximately 50% kill was achieved. The latter level is listed as the $LD_{50}$ for this group.

The primary screening level in each of the above tests was selected for purposes of convenience only, and none of the figures in the table are to be understood as representing the highest level at which a viable test for insecticidal activity can be conducted. Dashes are used in Table II where no tests were performed at all.

formulated mixtures can be applied to any habitat of the pests. Examples of such habitats are insect dwellings, clothing, plant surfaces, and soil. If desired, however, the active compositions can be applied directly to organic matter, seeds or feedstuffs in general, upon which the pests feed, or directly to the pests themselves. When applied in such a manner, it will be advantageous to use a formulation which is not volatile.

Particularly preferred compositions are those comprising an insecticidally effective amount of the active compound in combination with an inert insoluble solid carrier vehicle. Examples of such compositions are wettable powders, dusts, and flowable formulations, in which the solid carrier is in finely divided form; and granular formulations, in which the solid carrier is a pre-formed granule.

The amount of active compound or formulation which is considered to be insecticidally effective is that amount which, when applied to the pest habitat or feedstuff, will kill or substantially injure a significant portion residing or feeding thereon. The active compounds of this invention can be employed either as the sole pesticide component of the formulations or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the

TABLE II

| Example | Insecticide Activity — Approximate $LD_{50}$ Values | | | | | | | | |
|---|---|---|---|---|---|---|---|---|---|
| | HF μg | LB % | BBA % | GPA % | SMC % | CL % | TBW % | 2SM % (1) | (2) |
| 1 | 75 | >.05 | .005 | .003 | .008 | .002 | .02 | .0003 | .002 |
| 2 | 90 | >.05 | >.05 | — | .05 | .001 | .02 | .001 | .002 |
| 3 | >100 | .05 | .002 | .002 | .005 | .003 | .1 | .002 | .03 |
| 4 | >100 | .008 | .002 | .005 | .003 | .005 | .03 | .002 | .03 |

Symbols for Table II
HF : housefly
LB : Lygus bug
BBA : black bean aphid
GPA : green peach aphid
SMC : salt-marsh caterpillar
CL : cabbage looper
TBW : tobacco budworm
2SM : two-spotted mite - (1) post-embryonic
(2) eggs
> : greater than The compounds of this invention are generally used in formulations suitable for convenient application. In general, such formulations will contain inert or occasionally active ingredients or diluent carriers in addition to the active compound. Examples of such ingredients or carriers are organic solvents, such as sesame oil, xylene range solvents, and heavy petroleum; water; emulsifying agents; surface active agents, talc; pyrophyllite; diatomite, gypsum; clays; and propellants, such as dichlorodifluoromethane.

The active compounds can further be combined with dust carriers for application as dusts, with granular carriers for application by fertilizer spreaders or ground or airplane seeders, with wettable powders or flowable carriers for application as water suspensions, or with solvents and surface active materials for application as sprays, aerosols, or emulsions. The compounds or their preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the pesticide composition will comprise not more than about 50.0% by weight of the formulation.

What is claimed is:

1. A method of controlling insects comprising applying to said insects an insecticidally effective amount of a compound having the formula

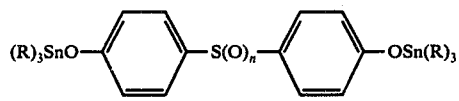

in which R is cyclohexyl or alkyl having 2 to 6 carbon atoms, and $n$ is 0, 1, or 2.

2. A method according to claim 1 in which R is cyclohexyl or alkyl having 2 to 6 carbon atoms, and $n$ is 0.

3. A method according to claim 1 in which R is cyclohexyl and $n$ is 0, 1, or 2.

4. A method according to claim 1 in which R is n-butyl and $n$ is 0.

5. A method according to claim 1 in which R is n-butyl and $n$ is 2.

6. A method according to claim 1 in which R is cyclohexyl and $n$ is 2.

7. A method according to claim 1 in which R is cyclohexyl and $n$ is 0.

* * * * *